(12) United States Patent
Gustin

(10) Patent No.: US 10,736,869 B2
(45) Date of Patent: Aug. 11, 2020

(54) COMPOSITIONS AND METHODS RELATED TO CANNABINOIDS, TERPENOIDS AND ESSENTIAL OILS

(71) Applicant: John C Gustin, Carlsbad, CA (US)

(72) Inventor: John C Gustin, Carlsbad, CA (US)

(73) Assignee: ECS Health Sciences, Inc., Carlsbad, CA (US)

( * ) Notice: Subject to any disclaimer, the term of this patent is extended or adjusted under 35 U.S.C. 154(b) by 0 days.

(21) Appl. No.: 16/509,453

(22) Filed: Jul. 11, 2019

(65) Prior Publication Data
US 2020/0038366 A1    Feb. 6, 2020

Related U.S. Application Data

(60) Provisional application No. 62/698,825, filed on Jul. 16, 2018.

(51) Int. Cl.
| | | |
|---|---|---|
| *A61K 36/00* | (2006.01) | |
| *A61K 31/352* | (2006.01) | |
| *A61K 31/047* | (2006.01) | |
| *A61K 47/44* | (2017.01) | |
| *A61K 36/537* | (2006.01) | |
| *A61K 36/258* | (2006.01) | |

(52) U.S. Cl.
CPC .......... *A61K 31/352* (2013.01); *A61K 31/047* (2013.01); *A61K 36/258* (2013.01); *A61K 36/537* (2013.01); *A61K 47/44* (2013.01)

(58) Field of Classification Search
CPC ..................................................... A61K 36/00
USPC ......................................................... 424/725
See application file for complete search history.

(56) References Cited

U.S. PATENT DOCUMENTS

2017/0008868 A1    1/2017   Dialer et al.

FOREIGN PATENT DOCUMENTS

WO    WO 2018023164    *    2/2018

\* cited by examiner

*Primary Examiner* — Michael V Meller

(57) ABSTRACT

The present invention provides cannabinoid and terpenoid compositions, among others, and methods of use including as medicines, supplements and nutraceuticals.

1 Claim, No Drawings

COMPOSITIONS AND METHODS RELATED TO CANNABINOIDS, TERPENOIDS AND ESSENTIAL OILS

BACKGROUND OF THE INVENTION

The present invention is in the technical fields of biochemistry and medicine. More particularly, the present invention is in the technical field of cannabinoid and terpene biochemistry, supplementation, medicinal therapy and nutraceutical therapy.

Cannabis is known in the art to produce many chemical compounds including cannabinoid and terpenoid compounds.

SUMMARY OF THE INVENTION

Embodiments of the present invention provide compositions and formulations of cannabinoids and terpenoids without or substantially without tetrahydrocannabinol (THC) compounds. Certain embodiments provide synthetic or extracted cannabinoids, synthetic terpenoids or both and embodiments that include: compositions, formulations, medicines, supplements and nutraceuticals. Certain embodiments provide methods of use of embodied compositions, formulations, medicines, supplements and nutraceuticals to assist people or other animals having pain, inflammation or both. Additional compositions, administrations combinations and methods of use are provided in embodiments herein.

BRIEF DESCRIPTION OF THE INVENTION

Certain embodiments of the present invention provide a composition, comprising: a combination of one or more synthetic cannabinoids and one or more synthetic terpenoids; wherein the composition substantially lacks a tetrahydrocannabinol. In certain embodiments, the composition contains less then 3% by volume, weight or both of a tetrahydrocannabinol compound and preferably, less than 2% or more preferably less than 1% of the tetrahydrocannabinol compound. In certain preferred embodiments, the instant composition does not include any non-synthetic compounds. In certain preferred embodiments, the synthetic compounds of the instant composition are at least one synthetic step removed from a naturally occurring source. For example, a precursor compound can be isolated from a naturally occurring source and is reacted chemically to form a synthetic compound of the instant composition.

In certain embodiments, the use of the antecedent "a" before an item refers to one or more of the items being referenced, including in the claims.

In certain embodiments, each cannabinoid and each terpenoid compound present in a composition are synthetic compounds.

In certain embodiments, compositions of the present invention contain nearly undetectable or undetectable amounts of a tetrahydrocannabinol compound.

In certain embodiments, compositions of the present invention include an excipient. In certain embodiments, the excipient comprises a pharmaceutically acceptable excipient or one acceptable for use in supplements, food supplements and/or nutraceuticals.

In certain embodiments, compositions of the present invention include a myrcene compound. In certain embodiments, the myrcene compound is a synthetic myrcene compound. In certain embodiments, a synthetic myrcene compound and one or more synthetic cannabinoids are combined in a composition, which composition may or may not include additional components, synthetic or non-synthetic; depending on the embodiment. In certain embodiments, the myrcene compound is isolated from an essential oil or extract of a plant.

In certain embodiments, compositions of the present invention include a caryophyllene compound. In certain embodiments, the caryophyllene compound is a caryophyllene oxide compound. In certain embodiments, the caryophyllene compound is a synthetic caryophyllene compound. In certain embodiments, a synthetic caryophyllene compound and one or more synthetic cannabinoids are combined in a composition, which composition may or may not include additional components, synthetic or non-synthetic; depending on the embodiment. In certain embodiments, the caryophyllene compound is isolated from an essential oil or extract of a plant.

In certain embodiments, compositions of the present invention include one or more cannabinoids present in an amount of 5% or greater by volume, weight or both. In certain preferred embodiments, the amount is 7% or more and, more preferably 10% or more by volume, weight or both.

In certain embodiments, compositions of the present invention include one or more terpenoids present in an amount of 3% or greater by volume, weight or both. In certain preferred embodiments, the amount is 5% or more, more preferably 7% or more and still more preferably 10% or more by volume, weight or both.

In certain embodiments, compositions of the present invention include one or more cannabinoids present in an amount of 10 mg or more (for each cannabinoid or for total cannabinoid content, depending on the embodiment). In certain preferred embodiments, the amount is 15 mg or more and, more preferably 20 mg or more (each cannabinoid or in combination, depending on the embodiment).

In certain embodiments, compositions of the present invention include one or more terpenoids are present in an amount of 5 mg or more (for each terpenoid or for total terpenoid content, depending on the embodiment). In certain preferred embodiments, the amount is 7.5 mg or more, more preferably 10 mg or more, and still more preferably 15 mg or more (each terpenoid or in combination, depending on the embodiment).

In certain embodiments, the formulation, comprises: an isolated cannabidiol (CBD) or a synthetic CBD and an essential oil of a plant, wherein the plant comprises (or alternately, consists essentially of): howood, rosewood, coriander, linaloe, sweet basil linalool type, thyme linalool type or cardamom or combinations and/or numbers thereof. In certain embodiments, the formulation, comprises: an isolated CBD. In certain embodiments, an isolated CBD refers to an extract that contains at least 80% CBD. In certain embodiments, an isolated CBD refers to an extract that contains at least 90% CBD. In certain embodiments, an isolated CBD refers to an extract that contains at least 95% CBD. In certain embodiments, an isolated CBD refers to an extract that contains at least 99% CBD.

In certain embodiments, the formulation, comprises: a synthetic CBD, a synthetic cannabinol (CBN) or a synthetic cannabigerol (CBG) or a mixture or combination thereof including combinations of two or three or more cannabinoids (which, in certain preferred embodiments, lacks or substantially lacks a tetrahydrocannabinol (THC)). In certain embodiments, the formulation, comprises: a combination of one or more cannabinoid extracts or isolates and at least one synthetic cannabinoid (preferably the formulation lacks or substantially lacks a tetrahydrocannabinol.

In certain embodiments, an isolated compound included in, or added to, a composition of the present invention (alternatively as an extract), refers to the compound being at least 50% of an extract by weight, volume or both. In increasing order of preferability, the compound makes up at least 70%, 80%, 90%, 95% or 99% of the extract by weight, volume or both.

In certain embodiments, the formulation, comprises: a CBD extract or isolate, a CBN extract or isolate, or a CBG extract or isolate or a mixture or combination thereof including combinations of two or three or more cannabinoids; and, in certain preferred embodiments, substantially lacks a tetrahydrocannabinol (THC).

In certain embodiments, the percent of a compound contained in an oil or extract of a plant, is determined by as a percentage of the total volume, weight or both.

In certain embodiments, the formulation is used as a fragrance or scent, for example, in an aroma therapy product. In certain embodiments, a formulation of the present invention is used in a beauty product, such as for hair or skin.

In certain embodiments, the formulation, comprises: an essential oil of a howood plant (in a preferred example, *Cinnamomum camphora*). In certain embodiments, the formulation contains a terpenoid isolated from an essential oil or extract of a howood plant.

In certain embodiments, the formula includes an essential oil or extract of a rosewood plant or an isolated terpenoid from a rosewood plant, preferably *Aniba rosaeodora*.

In certain embodiments, the formula includes an essential oil or extract of a coriander plant or an isolated a terpenoid from a rosewood, preferably *Coriandrum sativum L.*

In certain embodiments, the formulation, comprises: an essential oil of linaloe or a bark from a Bursera plant.

In certain embodiments, the formulation, comprises: an essential oil of sweet basil linalool type.

In certain embodiments, the formulation, comprises: an essential oil of thyme linalool type.

In certain embodiments, the formulation, comprises: an essential oil of cardamom.

In certain embodiments, the formulation, comprises: a combination of more than one essential oils. In certain embodiments, the formulation, comprises: a combination of more than one synthetic terpenoids. In certain embodiments, the formulation, comprises: a combination of one or more essential oils containing terpenoids and at least one synthetic terpenoid.

In certain embodiments, the formulation, comprises: an isolated cannabidiol (CBD), cannabinol (CBN), cannabigerol (CBG), or tetrahydrocannabinoid (THC), or a synthetic CBD, CBN, CBG or THC, and an essential oil a lavender plant.

In certain embodiments, the formulation, comprises: an isolated cannabinoid (CBD, CBN, CBG or THC). In certain embodiments, an isolated cannabinoid refers to an extract that contains at least 80% cannabinoid. In certain embodiments, an isolated cannabinoid refers to an extract that contains at least 90% cannabinoid. In certain embodiments, an isolated cannabinoid refers to an extract that contains at least 95% cannabinoid. In certain embodiments, an isolated cannabinoid refers to an extract that contains at least 99% cannabinoid.

In certain embodiments, the formulation, comprises: a synthetic cannabinoid (e.g., one or more of CBD, CBN, CBG or THC).

In certain embodiments, the formulation includes one or more of a CBD, CBN or CBG, but is substantially free of a THC (optionally, does not include a detectible amount of THC or the amount of THC is less than 0.5 mg or 0.5% by weight, volume or both of the formulation).

In certain embodiments, the formula includes an isolated or synthetic Myrcene (a terpenoid).

In certain embodiments, the formula includes an isolated or synthetic linalool (a terpenoid).

Embodiments Including THCs

In certain embodiments, a formulation is optionally substantially free of tetrahydrocannabinoid compounds (THCs). In certain embodiments, the THCs are present in the formula in less than 3%, 1%, 0.5%, 0.3% or 0.1% by volume, weight or both (preferably by dry weight). In certain embodiments, a formulation contains only a chemical trace of THC compounds. In certain embodiments, a formulation does not contain detectable THC compounds.

Embodiments Including Myrcene

In certain embodiments, the formulation comprises (or further comprises) a myrcene compound. In certain embodiments, wherein plant extracts are used in a formulation; the formulation further comprises an additive containing or being a myrcene compound. In certain embodiments, a myrcene terpene is included in the formulation to enhance the uptake of the formulation into the brain through the blood brain barrier.

EXAMPLES

Example 1

Certain embodiments include myrcene, preferable β-myrcene, which is a monoterpene and a common terpene produced by cannabis (some varieties contain up to 60% of the essential oil). Myrcene is found in the essential oil of hops, citrus fruits, bay leaves, eucalyptus, wild thyme, lemon grass and many other plants.

In certain embodiments, myrcene comprises one or more medicinal properties, including lowering the resistance across the blood to brain barrier, allowing itself and many other chemicals to cross the barrier more easily and/or more quickly. In certain embodiments, myrcene is included to enhance the effects of one or more cannabinoids, preferably enhancing a more rapid onset of cannabinoid effects. In certain embodiments, myrcene is included in a formulation of the present to increase the maximum saturation level of the CB1 receptor, allowing for a greater maximum psychoactive effect for THC.

In certain embodiments, myrcene is included in a formulation as a fragrance agent, preferably providing a scent of musky, earthy or herbal aromas.

Certain embodiments comprising a myrcene compound are useful as an analgesic, anti-inflammatory, antibiotic, antimutagenic or a combination thereof. Certain embodiments comprising a myrcene compound are useful for inhibition of cytochrome, aflatoxin B and other pro-mutagenic carcinogens. Certain embodiments comprising a myrcene compound are useful for treating gastric and duodenal ulcers or alleviating symptoms thereof in a subject or person in such need. Certain embodiments comprising a myrcene compound are useful for sedative and relaxing effects in a subject or person in need thereof. Certain embodiments comprising a myrcene compound are useful for treating insomnia or alleviating symptoms thereof in a subject or person in such need. Certain embodiments comprising a myrcene compound are useful for treating pain or alleviating symptoms of pain in a subject or person in such need. Certain embodiments comprising a myrcene compound are useful for treating inflammation or alleviating symptoms of inflammation in a subject or person in such need.

Example 2

Certain embodiments include linalool, which is a non-cyclic monoterpene. Certain embodiments comprising a linalool compound are useful for treating inflammation or alleviating symptoms of inflammation in a subject or person in such need. Certain embodiments comprising a linalool compound are useful for treating pain or alleviating symptoms of pain in a subject or person in such need. Certain embodiments comprising a linalool compound are useful for promoting calm and relaxation or for treating anxiety or for alleviating symptoms of anxiety in a subject or person in such need. Certain embodiments comprising a linalool compound are useful for promoting sleep or treating a sleep disturbance such as insomnia or alleviating symptoms of a sleep disturbance in a subject or person in such need. In certain embodiments, linalool is included in a formulation as a fragrance agent, preferably providing a scent of floral, especially lavender, aromas.

Linalool can be extracted from the Lamiaceae, Rutaceae, Lauraceae plant families, which include, for example: mints, laurels, cinnamon, rosewood and citrus plants. Linalool can also be extracted from birch and certain fungi.

Example 3

Certain embodied examples provide for pain relief in a subject or person in need of pain relief or for the alleviation of symptoms of pain using a formulation as follows.

Formula for Example 3

A formulation, comprising: one or more cannabinoids being CBD, CBN and/or CBG and one or more terpenoids including linalool. The formulation optionally further includes THC, but preferably lacks detectable levels of THC or has an insubstantial amount of THC (for example, a non-psychoactive amount). The formulation preferably includes at least one synthetic cannabinoid and/or at least one synthetic terpenoid.

Example 4

Certain embodied examples provide for pain relief in a subject or person in need of pain relief or for the alleviation of symptoms of pain using a formulation as follows.

Formula for Example 4

A formulation, comprising: one or more cannabinoids being CBD, CBN and/or CBG and one or more terpenoids including myrcene. The formulation optionally further includes THC, but preferably lacks detectable levels of THC or has an insubstantial amount of THC (for example, a non-psychoactive amount). The formulation preferably includes at least one synthetic cannabinoid and/or at least one synthetic terpenoid.

Example 5

Certain embodied examples provide for pain relief in a subject or person in need of pain relief or for the alleviation of symptoms of pain using a formulation as follows.

Formula for Example 5

A formulation, comprising: one or more cannabinoids being CBD, CBN and/or CBG and one or more terpenoids including caryophyllene (preferably caryophyllene oxide). The formulation optionally further includes THC, but preferably lacks detectable levels of THC or has an insubstantial amount of THC (for example, a non-psychoactive amount). The formulation preferably includes at least one synthetic cannabinoid and/or at least one synthetic terpenoid.

Example 6

Certain embodied examples provide for pain relief in a subject or person in need of pain relief or for the alleviation of symptoms of pain using a formulation as follows.

Formula for Example 6

A formulation, comprising: a CBD cannabinoid and one or more terpenoids, preferably a caryophyllene, a myrcene and/or a linalool. The formulation optionally further includes THC, but preferably lacks detectable levels of THC or has an insubstantial amount of THC (for example, a non-psychoactive amount). The formulation preferably includes at least one synthetic cannabinoid and/or at least one synthetic terpenoid.

Example 7

Certain embodied examples provide for pain relief in a subject or person in need of pain relief or for the alleviation of symptoms of pain using a formulation as follows.

Formula for Example 7

A formulation, comprising: a CBN cannabinoid and one or more terpenoids, preferably a caryophyllene, a myrcene and/or a linalool. The formulation optionally further includes THC, but preferably lacks detectable levels of THC or has an insubstantial amount of THC (for example, a non-psychoactive amount). The formulation preferably includes at least one synthetic cannabinoid and/or at least one synthetic terpenoid.

Example 8

Certain embodied examples provide for pain relief in a subject or person in need of pain relief or for the alleviation of symptoms of pain using a formulation as follows.

Formula for Example 8

A formulation, comprising: a CBG cannabinoid and one or more terpenoids, preferably a caryophyllene, a myrcene and/or a linalool. The formulation optionally further includes THC, but preferably lacks detectable levels of THC or has an insubstantial amount of THC (for example, a non-psychoactive amount). The formulation preferably includes at least one synthetic cannabinoid and/or at least one synthetic terpenoid.

Example 9

Certain embodied examples provide for pain relief in a subject or person in need of pain relief or for the alleviation of symptoms of pain using a formulation as follows.

Formula for Example 9

A formulation, comprising: a THC cannabinoid and one or more terpenoids, preferably a caryophyllene, a myrcene and/or a linalool. The formulation optionally further includes a CBD. The formulation preferably includes at least one synthetic cannabinoid and/or at least one synthetic terpenoid.

Example 10

Certain embodied examples provide for pain relief in a subject or person in need of pain relief or for the alleviation of symptoms of pain using a formulation as follows.

Formula for Example 10

A formulation, comprising: a THC cannabinoid and one or more terpenoids, preferably a caryophyllene, a myrcene and/or a linalool. The formulation optionally further includes a CBN cannabinoid, but preferably lacks detectable levels of a CBD cannabinoid or has an insubstantial amount of CBD cannabinoid present in the formulation. The formulation preferably includes at least one synthetic cannabinoid and/or at least one synthetic terpenoid.

Example 11

Certain embodied examples provide for pain relief in a subject or person in need of pain relief or for the alleviation of symptoms of pain using a formulation as follows.

Formula for Example 11

A formulation, comprising: a THC cannabinoid and one or more terpenoids, preferably a caryophyllene, a myrcene and/or a linalool. The formulation optionally further includes a CBG cannabinoid, but preferably lacks detectable levels of a CBD cannabinoid or has an insubstantial amount of CBD cannabinoid present in the formulation. The formulation preferably includes at least one synthetic cannabinoid and/or at least one synthetic terpenoid.

Example 12

A formulation of the present invention is administered by including carriers for vaping in the formulation (for example: propylene glycol, vegetable glycerin or both) and the subject (being a person in this example) inhales the formulation by vaping. Preferably, the subject inhales an amount sufficient to provide the subject with the desired effect (e.g., relaxation), treatment (e.g., reduced pain), therapy or alleviation of a symptom.

Example 13

A formulation of the present invention is combined with a transdermal permeation enhancer, a transdermal patch or a combination thereof and is applied to a skin of the subject. Preferably, an amount of the formulation is applied via the transdermal route sufficient to provide the subject with the desired effect (e.g., relaxation), treatment (e.g., reduced pain, reduced inflammation), therapy or alleviation of a symptom.

Example 14

A formulation of the present invention is provided in an intranasal spray, metered dose device or intranasal administration device and administered to the nasal cavity or by insufflation by the subject. Preferably, an amount of the formulation is applied via the intranasal route sufficient to provide the subject with the desired effect (e.g., relaxation), treatment (e.g., reduced pain, reduced inflammation), therapy or alleviation of a symptom.

Example 15

A formulation of the present invention is provided in a food or a dietary supplement for ingestion by a subject. Preferably, an amount of the formulation is provided in a serving of food or a serving of the dietary supplement to provide the subject with the desired effect (e.g., relaxation), treatment (e.g., reduced pain, reduced inflammation), therapy or alleviation of a symptom.

Example 16

A formulation of the present invention is provided as a nutraceutical or in a nutraceutical composition for use by a subject by a subject. Preferably, an amount of the formulation is provided in a dose or serving of the nutraceutical to provide the subject with the desired effect (e.g., relaxation), treatment (e.g., reduced pain, reduced inflammation), therapy or alleviation of a symptom.

Certain preferred embodiments of the present invention are not bound by a described mechanism of action.

Certain embodiments provide a product substantially as hereinbefore including as described in one or more embodiments or combination of embodiments and/or by reference to an example, figure, table or drawing.

What is claimed is:

1. A mixture of synthetic cannabigerol, synthetic myrcene, a component selected from the group consisting of howood, coriander, linaloe, sweet basil, and thyme, a component selected from the group consisting of ginseng and sage, and a component selected from the group consisting of valerian and lavender.

* * * * *